US00PP10698P

United States Patent [19]

McGredy

[11] Patent Number: Plant 10,698

[45] Date of Patent: Nov. 24, 1998

[54] HYBRID TEA ROSE PLANT NAMED 'MACKATI'

[75] Inventor: Sam McGredy, Auckland, New Zealand

[73] Assignee: DeVor Nurseries, Inc., Watsonville, Calif.

[21] Appl. No.: 742,145

[22] Filed: Oct. 31, 1996

[51] Int. Cl.[6] ..... A01H 5/00

[52] U.S. Cl. ..... Plt./21

[58] Field of Search ..... Plt./11, 20, 22, Plt./28, 29, 21

[56] References Cited

PUBLICATIONS

UPOVROM Plant Variety Database, 1997 Mar., GTI Jouve Retrieval Software, Listings for 'Mackati'.

*Primary Examiner*—Howard J. Locker
*Attorney, Agent, or Firm*—Christie, Parker & Hale, LLP

[57] ABSTRACT

A hybrid tea rose variety producing red purple flowers.

1 Drawing Sheet

BACKGROUND OF THE INVENTION

The present invention relates to a new and distinct hybrid tea rose variety which was originated by my crossing as seed parent the variety known as 'Macsupple' and as pollen parent the variety known as 'Big Purple.' The varietal denomination of this new rose is 'Mackati.'

SUMMARY OF THE INVENTION

Among the novel characteristics possessed by the new variety which distinguish it from its parents and all other varieties of which I am aware are its attractive, many-petaled, red purple flowers borne on a bushy, vigorous thornless plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

Comparison with Parents

'Macsupple' is a tall floribunda producing purple flowers in tight trusses; 'Mackati' produces "old rose"—type blooms of lighter color. 'Big Purple' produces large deep purple flowers with strong scent on stems with thorns; the new variety produces flowers with less scent on vertically thornless stems.

BRIEF DESCRIPTION OF ILLUSTRATION

The accompanying illustration show typical specimens of the vegetative growth and flowers of the new variety in different stages of development and depicted in color as nearly true as it is reasonably possible to make the same in a color illustration of this character.

BRIEF DESCRIPTION OF THE NEW VARIETY

Parentage: Seedling.
*Seed parent.*—'Macsupple'.
*Pollen parent.*—'Big Purple'.
Class: Hybrid Tea.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

1. Flower

Blooming habit: Continuous.

A. Bud:
- (1) *Size.*—Small; about 3 to 3.5 cm long and wide.
- (2) *Form.*—Globose.
- (3) *Color.*—When sepals first divide, bud color is near 59C.
- (4) *Sepals.*—Lanceolate, about 2.4 cm, barely covering bud, sepals are upright then reflex, top side blushed near 174A, underside somewhat lighter. Color: Light green.
- (5) *Peduncle.*—Length: About 3 cm to about 5 cm. Aspect: Smooth. Strength: Erect. Color: Near 146D with reddish blush, near 182A.
- (6) *Bracts.*—About 1 or 2, broadly elliptical with long apex, margin ciliate, about 3.5 to 4.5 cm below flower.

B. Bloom:
- (1) *Size.*—Average size when fully expanded — about 9 cm to about 11 cm.
- (2) *Borne.*—Singly.
- (3) *Form.*—Quartered at maturity.
- (4) *Petalage.*—Number of petals under normal conditions — about 45 to 50.
- (5) *Color* (⅓–½ *open*).—Outer petals — Top surface: near 61A; Undersurface: near 59B. Inner petals — Top surface: near 61A; Undersurface: near 59B. Base of petals: Near 150B. General tonality from a distance: Red purple .
- (6) *Color* (*Fully open*).—Outer petals — Top surface: near 64A with veining of near 71A; Undersurface: near 59C with veining of near 71B. Inner petals — Top surface: near 64A with veining near 71A Undersurface: near 59C with veining near 71A. Base of petals: Near 1D. General tonality from a distance: Red purple.
- (7) *Color change.*—Color lightens from a dark red-purple to a little lighter red purple coloration and with a little more blue veining of petals. Petal top surface: Lightens very slightly. Petal undersurface: Remains constant. General tonality at a distance: Red purple.

C. Petals:
(1) *Texture.*—Thick, smooth.
(2) *Appearance.*—Inside slightly velvety and outside matte.
(3) *Form.*—Elliptic.
(4) *Arrangement.*—Imbricated and quartered.
(5) *Petaloids.*—Average about 6 to 7.
(6) *Persistence.*—Petals drop off cleanly.
(7) *Fragrance.*—Old rose fragrance.
(7) *Lasting quality.*—On plant about 10 to 12 days; about 6 to 8 days after cutting.

2. Reproductive Organs

A. Stamens:
(1) *Arrangement.*—Regularly arranged around styles.
(2) *Anthers.*—Color — near 22A.
(3) *Filaments.*—Color — near 27C.
(4) *Pollen.*—Color — near 22A.

B. Pistils:
(1) *Styles.*—Bunched.
(2) *Stigmas.*—Color — near 4C.

C. Characteristics of hips: Globose, about 2 cm wide by about 2 cm long, near 146B with tinges of near 163B toward top of hip.

Plant

A. Form: Medium, compact, upright.

B. Growth: Vigorous but compact; about 70 cm to about 76 cm in height and about 60 cm to 69 cm width at first season.

C. Foliage: Compound 3 to 5 leaflets.
(1) *Size.*—Medium; about 8 to 12 cm long, about 6 to 11 cm wide.
(2) *Quantity.*—Abundant.
(3) *Color.*—New foliage — upper and lower near 182A; mature foliage — upper side near 147A, underside near 147B.
(4) *Shape.*—Ovate.
(5) *Texture.*—Upper side leathery, semi-glossy; underside leathery, matte.
(6) *Edge.*—Serrate.
(7) *Serration.*—Denticulate.
(8) *Leaf stem.*—Color — medium green.
(9) *Stipules.*—Parallel, middle enlarged, slightly bearded.
(10) *Rachis.*—Smooth.
(11) *Petioles.*—Top near 146A, underside near 144A.
(12) *Auricle.*—Medium, pointed, curving slightly downward.
(13) *Resistance to disease.*—Moderate resistance to mildew, rust and blackspot.

D. Wood:
(1) *New wood.*—Color near 146A, bark smooth.
(2) *Old wood.*—Color near 146A, bark smooth.

E. Flower stem: About 26 cm to about 31 cm from last cut.

F. Thorns:
(1) *Thorns.*—Quantity: None.

G. Winter hardiness: Winter hardy in Watsonville, Calif.

I claim:

1. A new and distinct variety of hybrid tea rose plant, substantially as shown and described.

* * * * *

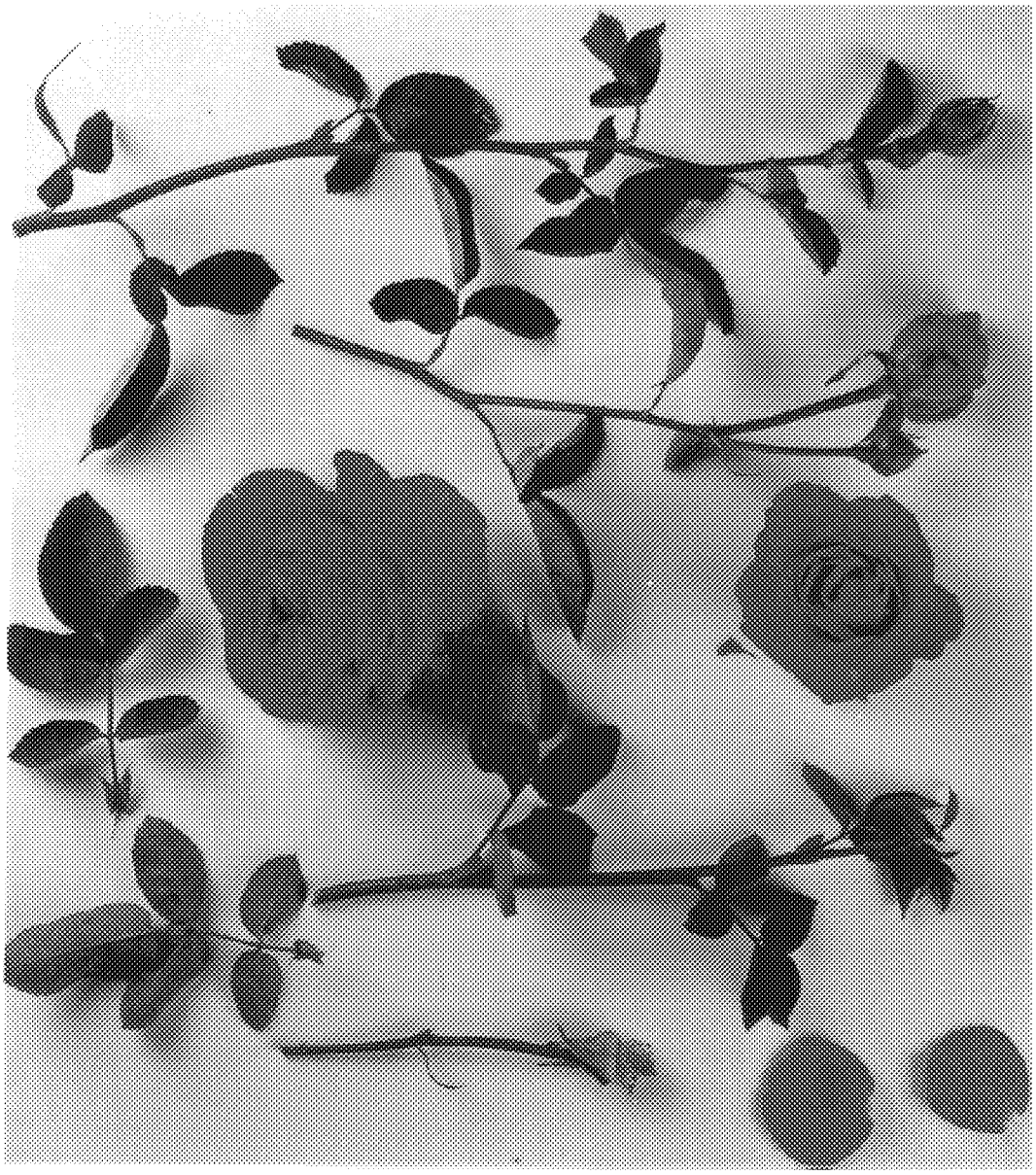

UNITED STATES PATENT AND TRADEMARK OFFICE

CERTIFICATE OF CORRECTION

PATENT NO. : Plant 10,698
DATED : November 24, 1998
INVENTOR(S) : Sam McGredy

It is certified that error appears in the above-identified patent and that said Letters Patent is hereby corrected as shown below:

Column 3, line 31, before "Plant" insert -- 3. --.

Signed and Sealed this
First Day of February, 2000

*Attest:*

*Attesting Officer*

Q. TODD DICKINSON

*Acting Commissioner of Patents and Trademarks*